United States Patent [19]

Petty

[11] 4,199,527

[45] Apr. 22, 1980

[54] REMOVAL OF KETENE IMPURITIES IN THE PREPARATION OF ALPHA-CYANO-ARYLOXYBENZYL ALCOHOLS

[75] Inventor: Walter L. Petty, Houston, Tex.

[73] Assignee: Shell Oil Company, Houston, Tex.

[21] Appl. No.: 957,264

[22] Filed: Nov. 2, 1978

[51] Int. Cl.[2] .................... C07C 120/00; C07C 121/75

[52] U.S. Cl. ............................ 260/465 D; 260/544 D; 260/585.5

[58] Field of Search .......................... 260/465 D, 585.5

[56] References Cited

U.S. PATENT DOCUMENTS

| | | | |
|---|---|---|---|
| 2,369,919 | 2/1945 | Sauer | 260/585.5 |
| 3,835,176 | 9/1974 | Matsuo et al. | 260/465 D |
| 4,110,360 | 8/1978 | Sheldon et al. | 260/465 D |

OTHER PUBLICATIONS

Lecher et al., Chemical Abstracts, vol. 40, 1869 (1945).
Yakubovich et al., Chemical Abstracts, vol. 43, 564 (1948).
Jochem et al., Chemical Abstracts, vol. 77, 87907n (1972).

*Primary Examiner*—Dolph H. Torrence

[57] ABSTRACT

An improved process for preparation of insecticidal esters of alpha-cyano-m-aryloxybenzyl alcohols is disclosed which includes the steps of preparing an acid chloride of the formula:

$$\text{Y-C}_6\text{H}_4\text{-C(R)(H)-C(=O)-Cl}$$

by reacting the corresponding acid with thionyl chloride, purifying the acid chloride thus obtained by fractional distillation and reacting the purified acid chloride with a phenoxybenzaldehyde and a cyanide solution to yield the desired insecticidal product. In this improved process, the presence of difficult to remove ketene reaction products in the final insecticidal product is avoided by treating the purified acid chloride with an ahydrous hydrogen halide prior to reaction with the phenoxybenzaldehyde.

5 Claims, No Drawings

REMOVAL OF KETENE IMPURITIES IN THE PREPARATION OF ALPHA-CYANO-ARYLOXYBENZYL ALCOHOLS

BACKGROUND OF THE INVENTION

This invention relates to an improved process for preparation of certain insecticidal esters of alpha-cyano-m-aryloxybenzyl alcohols known conventionally as synthetic pyrethroids. More particularly, this invention is directed to an improvement in the stepwise synthesis of such esters in which a distilled acid chloride intermediate is treated with an anhydrous hydrogen halide to obviate the formation of undesirable impurities in the final insecticidal product obtained on reaction of the acid chloride with a phenoxybenzaldehyde and a cyanide solution.

Esters of alpha-cyano-m-aryloxybenzyl alcohols are disclosed in U.S. Pat. No. 4,062,968 as being superior insecticides for certain economically important insects. In accordance with the disclosure in U.S. Pat. No. 4,056,509 the esters are prepared using 2-(4-chlorophenyl)-3-methyl butanoyloxy compounds, which in turn have been prepared via the hydrolysis of the alkylated benzyl cyanides also disclosed herein. Alternative methods for the preparation of the esters are disclosed in U.S. Pat. Nos. 4,110,360 to 4,110,363, inclusive.

One very suitable technique for preparing these esters proceeds stepwise through an acid chloride intermediate, said acid chloride being reacted with the appropriate phenoxybenzaldehyde in the presence of cyanide ion to yield the desired product. In this stepwise synthesis, the acid chloride intermediate is very conveniently prepared by reacting the corresponding acid with thionyl chloride. While this reaction affords high yields of the desired acid chloride intermediate, small quantities of by-products, e.g. heavy ends, are also produced which make it desirable to further purify this reaction product prior to reaction with the phenoxybenzaldehyde. For larger scale operations, fractional distillation is particularly suited for this purification step. In carrying out this distillation it has been found that while the acid chloride can be isolated in high yield and purity, there is formed and/or carried over from the chlorination, minor amounts of a ketene impurity which distills at the same conditions as the desired acid chloride. This ketene impurity is undesirable because it will subsequently react with the phenoxybenzaldehyde to produce a contaminant which is very difficult to remove from the final product. With the instant invention, a simple and effective technique has been devised to avoid formation of this undesirable ketene-derived impurity while retaining the benefits of the use of the distilled and purified acid chloride in the stepwise synthesis technique.

It is well known in the art that hydrogen halides add to ketenes to yield acid chlorides. However, until the present disclosure, the presence of a ketene as the cause of impurities in insecticidal esters prepared by reacting an acid chloride, a phenoxybenzaldehyde and a cyanide solution was unknown. Hydrogen chloride gas is used to treat p-thionylaminobenzoyl chloride to yield p-aminobenzoyl chloride hydrochloride in U.S. Pat. No. 3,597,475. Similarly, a p-aminobenzoic acid salt is prepared from p-aminobenzoic acid with anhydrous hydrogen chloride in U.S. Pat. No. 3,681,450. In a process for converting carboxylic acids to acid halides, Japanese Pat. No. 49,030,311 discloses the elimination of residual halogenating agent with water, monohydric or polyhydric alcohols, carboxylic acids or organic metal compounds.

The preparation of synthetic pyrethroids is disclosed in U.S. Pat. No. 4,062,968.

SUMMARY OF THE INVENTION

A process improvement has now been discovered by which the aforementioned synthetic pyrethroid insecticides can be synthesized in the substantial absence of troublesome ketene reaction products using acid chloride reactants which have been prepared from the corresponding acid by reaction with thionyl chloride and subsequently purified by distillation. This process improvement is based, in part, on the finding that the ketene precursor to the troublesome impurities is generated and/or carries through the acid chloride distillation and, in part, on the determination that it can be substantially removed, i.e. converted into the desired acid chloride, by the action of an anhydrous hydrogen halide without any adverse effect on the process.

The process itself consists of reacting an acid chloride represented by the general formula (I):

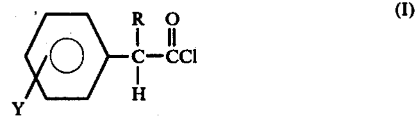

(I)

wherein R represents a secondary alkyl group of from 3 to 6 carbon atoms and Y represents a hydrogen atom or a halogen atom of atomic number 9 to 35, inclusive; with a phenoxybenzaldehyde and a cyanide solution, where the acid chloride is prepared by reacting the corresponding acid with thionyl chloride and subsequently purified by fractional distillation. During this distillation there is generated and/or carried over a ketene by-product of the general formula (II):

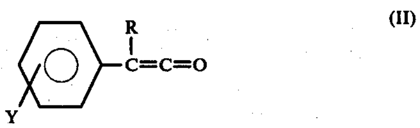

(II)

wherein R and Y have the same meaning as above. This ketene impurity reacts further with the cyanide solution to give contaminants which are very difficult to remove from the desired pyrethroid final product. In accordance with the invention, this ketene impurity is removed in a very simple and efficient manner by treating the distilled acid chloride with an anhydrous hydrogen halide prior to reaction with the phenoxybenzaldehyde.

Accordingly, the present invention provides an improved process for preparing insecticidal esters of alpha-cyano-m-aryloxybenzyl alcohols by the steps of preparing an acid chloride of the formula:

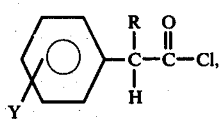

wherein R represents a secondary alkyl group of from 3 to 6 carbon atoms and Y represents a hydrogen atom or halogen atom of atomic number 9 to 35, inclusive, by reacting the corresponding acid with thionyl chloride, purifying the acid chloride thus obtained by fractional distillation and reacting the purified acid chloride with a phenoxybenzaldehyde and a cyanide solution to yield the desired insecticidal product, characterized in that the purified acid chloride is reacted with an anhydrous hydrogen halide under conditions which substantially convert the ketene impurity present in the purified acid chloride to the desired acid chloride, thereby avoiding further reaction of the ketene with said cyanide solution to yield an impurity which contaminates the desired insecticidal product.

DESCRIPTION OF THE PREFERRED EMBODIMENTS

Preferred acid chloride reactants of formula (I) above are those in which Y represents a halogen atom. Most preferably, Y represents a chlorine atom in the para position and R represents an isopropyl group. In this regard, the acid chloride reactants are structurally related to the acetonitrile compounds described in U.S. Pat. No. 4,056,509. The preferred phenoxybenzaldehyde reactant is m-phenoxybenzaldehyde and the preferred cyanide solution is an aqueous sodium cyanide solution. Anhydrous hydrogen chloride is the anhydrous hydrogen halide of choice.

The most preferred reactants in the process improvement claimed herein are thus alpha-isopropyl-p-chlorophenylacetyl chloride, m-phenoxybenzaldehyde and an aqueous sodium cyanide solution. Further, in the most preferred embodiment, anhydrous hydrogen chloride is used to convert the ketene impurities to the acid chloride. When the most preferred reactants described above are utilized to prepare a synthetic pyrethroid in the manner specified, the ketene impurity which is the focus of this invention will be of formula (II) in which Y represents a chlorine atom and R represents an isopropyl group.

The acid chlorides (I) employed in the process of the invention are suitably prepared by the following multistep synthesis. Firstly, the alkylated acetonitrile compounds prepared in U.S. Pat. No. 4,056,509 are hydrolyzed to disubstituted acetic acids as specified in U.S. Pat. No. 4,062,968. These disubstituted acetic acids are in turn halogenated with an excess of thionyl chloride or other suitable halogenating agent to yield the desired acid chlorides (I). When thionyl chloride is used, gaseous HCl and $SO_2$ evolve and are normally absorbed in a caustic scrubber. Before being passed to a distillation column, the reaction mixture is also customarily washed with water to remove residual gases and thionyl chloride.

The phenoxybenzaldehyde reactants are conveniently prepared via the bromination of a phenoxytoluene, resulting in a phenoxybenzyl bromide which yields the desired phenoxybenzaldehyde upon treatment with formaldehyde and ammonia. The final mixture is purified by distillation. The phenoxybenzaldehyde is normally present in an amount ranging from 0.9 to 1.1 moles per mole of the acid chloride (I).

The cyanide solution employed in the reaction between the acid chloride and the phenoxybenzaldehyde is preferably an aqueous sodium cyanide solution although various other alkali metal cyanides, such as an aqueous potassium cyanide solution, may be used. The cyanide solution may range in concentration from 1% to 30%, and is normally added so as to provide from 1.0 to 1.3 moles of the cyanide per mole of the acid chloride (I).

The acid chloride (I) and phenoxybenzaldehyde in a suitable organic solvent and the aqueous cyanide solution are allowed to react in an inert atmosphere until the reaction is essentially complete. Suitable organic solvents include such hydrocarbons as heptane, cyclohexane, toluene or mixtures thereof, with an aliphatic hydrocarbon such as heptane being the solvent of choice. A suitable phase transfer catalyst such as benzyltriethylammmonium chloride may be added and the reaction is suitably conducted at a temperature of from 0° to 50° C. Such a reaction is sometimes referred to as the Francis reaction. The desired insecticidal esters of alpha-cyano-m-aryloxybenzyl alcohols are removed or purified by conventional means, such as extraction or distillation.

The hydrogen halide used to treat the purified acid chloride in the improvement according to the invention is substantially anhydrous so as to minimize the reaction of the ketene by-product (II) with water which yields the acid counterpart of the acid chloride (I). The hydrogen halide is suitably contacted with the purified acid chloride at 0° to 100° C. until reaction is complete. While the hydrogen halide may be employed on an equimolar basis with the amount of ketene impurity present in the purified acid chloride, the molar ratio of hydrogen halide/ketene impurity is preferably greater than one to assure substantially complete conversion to acid chloride within short reaction times. This reaction takes place in a few minutes at room temperature. To remove any unreacted hydrogen halide, the mixture may be purged with inert gas, evacuated to subatmospheric pressure or washed with water.

Examples of the desirable insecticidal ester end products are of the formula (III):

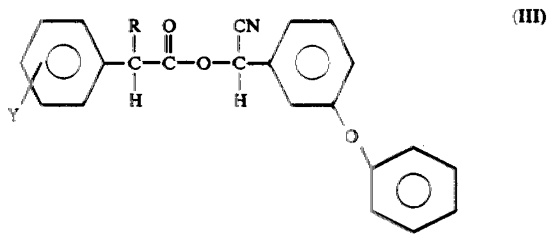

(III)

As mentioned above, this class of compounds is disclosed in U.S. Pat. No. 4,062,968. Without the process improvement of this invention, the ketene impurity generated and/or carried over in the distillation of the acid chloride (I) reacts further with the cyanide solution and contaminates the desired ester of the alpha-cyano-m-aryloxybenzyl alcohol with compounds whose structures are believed to be of the formula (IV):

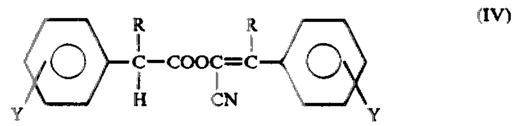

(IV)

The purification of the acid chloride reactant in the manner specified results in the reduction of the ketene by-product (II) to trace levels undetectable by infrared spectroscopy. The instant process improvement thus serves to reduce the amounts of contaminants believed to be of formula (IV) that later appear in the final product. While these contaminants commonly occurred at levels of from 0.7 to 5% in the esters prepared with the untreated acid chloride, they were reduced to levels of from 0.1 to 0.2% in the esters prepared with the acid chloride treated according to this invention. Thus, there is provided herein a simple technique to avoid the eventual formation in the desired insecticidal ester of contaminants otherwise very difficult to remove. This technique has no unfavorable effects on the overall process and permits the advantages of employing purified acid chlorides to be retained. The invention is illustrated further in the following examples.

EXAMPLE I

A wet solution of alpha-isopropyl-p-chlorophenylacetic acid (24.4%) in heptane was treated with an excess of thionyl chloride at 50°-60° C. for five hours. The hydrogen chloride and sulfur dioxide gases that evolved were absorbed in a caustic scrubber. Residual gases and thionyl chloride were washed from the reaction mixture by three water washes. The wet organic solution was then continuously distilled through a 2 inch by 60 inch column of ceramic packing. The distillation was performed at a pressure of 50 torr and a kettle temperature of 149° C. to reduce decomposition of the acid chloride. The dark bottoms product from this distillation was then batch distilled in three portions through a short Vigreux column at reduced pressure (20 torr down to 2 torr) with kettle temperature maintained so as to not exceed 155° C. An infrared spectrum of the third fraction showed that it contained approximately 2% of the ketene, arising from the thermal loss of hydrogen chloride from the alpha-isopropyl-p-chlorophenylacetyl chloride.

EXAMPLE II

Approximately 11 grams of the contaminated acid chloride from Example I was treated with anhydrous hydrogen chloride at room temperature for several minutes. The originally bright yellow liquid turned almost colorless. Excess hydrogen chloride was removed by purging the product with nitrogen gas and reducing the pressure to about 2 torr. An infrared spectrum of the product showed that the ketene had been completely converted to the acid chloride.

EXAMPLE III

Parallel experiments were performed where the contaminated acid chloride from Example I (estimated to contain 0.7% of the ketene at the time of this experiment) or the treated acid chloride from Example II was reacted with m-phenoxybenzaldehyde to form the synthetic pyrethroid. 2.00 Grams of m-phenoxybenzaldehyde and 2.52 grams of either acid chloride in heptane solvent were stirred together with 2.83 grams of aqueous sodium cyanide (20%) containing 0.006 grams of benzyltriethylammonium chloride catalyst. The reaction was allowed to proceed at room temperature under a nitrogen atmosphere for three hours. Gas chromatographic analysis of the products showed that the pyrethroid prepared with the contaminated acid chloride from Example I contained a total of approximately 0.4% of the impurities believed to be of formula (IV) above. Similar analysis of the products prepared using the treated acid chloride from Example II showed such impurities to be essentially absent.

EXAMPLE IV

2368 Grams of alpha-isopropyl-p-chlorophenylacetyl chloride prepared as in Example I was treated with anhydrous hydrogen chloride for 22 minutes at room temperature. Infrared analysis then indicated the absence of the ketene. This acid chloride and an equimolar amount of m-phenoxybenzaldehyde were charged to a reactor with heptane solvent (56.5%) and stirred. A 20% excess of aqueous sodium cyanide (15% by weight) and benzyltriethylammonium chloride catalyst was metered in for 1.9 hours at 30° C. The mixture was stirred at this temperature and monitored by gas chromatographic analysis for an additional 5 hours until conversion of the m-phenoxybenzaldehyde appeared complete at 99%. The mixture was warmed to 50° C. to solubilize the pyrethroid product, phase separated and the organic phased washed three times with water. The heptane was removed at 250° C. in a wiped-film-evaporator. Gas chromatographic analysis of the crude product showed that it contained only a total of 0.15% of the impurities believed to be of formula (IV).

What is claimed is:

1. In the process for the preparation of insecticidal esters of alpha-cyano-m-aryloxybenzyl alcohols by the steps of preparing an acid chloride of the formula:

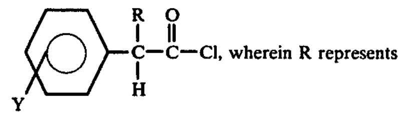

a secondary alkyl group of from 3 to 6 carbon atoms and Y represents a hydrogen atom or halogen atom of atomic number 9 to 35, inclusive, by reacting the corresponding acid with thionyl chloride, purifying the acid chloride thus obtained by fractional distillation and reacting the purified acid chloride with a phenoxybenzaldehyde and a cyanide solution to yield the desired insecticidal product, the improvement which comprises reacting the purified acid chloride with anhydrous hydrogen chloride under conditions which substantially convert a ketone impurity of the formula:

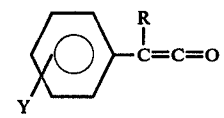

which is generated and/or carried over in said distillation and is present in the purified acid chloride to the desired acid chloride, thereby avoiding further reaction of the ketene with said cyanide solution to yield an impurity which contaminates the desired insecticidal product.

2. The improvement according to claim 1, in which Y is a chlorine atom.

3. The improvement according to claim 2, in which R is an isopropyl group.

4. The improvement according to claim 3, in which said phenoxybenzaldehyde is m-phenoxybenzaldehyde.

5. The improvement according to claim 4, in which said cyanide solution is an aqueous sodium cyanide solution.

* * * * *